United States Patent
Jost et al.

(10) Patent No.: US 6,410,916 B1
(45) Date of Patent: Jun. 25, 2002

(54) ROOM TEMPERATURE IR CAMERA

(75) Inventors: Steven Jost, Amherst, NH (US); Paul R. Murphy, Medford, MA (US)

(73) Assignee: BAE Systems Information and Electronic Systems Integration, Inc., Nashua, NH (US)

( * ) Notice: Subject to any disclaimer, the term of this patent is extended or adjusted under 35 U.S.C. 154(b) by 0 days.

(21) Appl. No.: 09/379,644

(22) Filed: Aug. 23, 1999

(51) Int. Cl.⁷ .................................................. G01J 5/00
(52) U.S. Cl. ...................................... 250/332; 250/349
(58) Field of Search ........................... 250/332, 338.4, 250/349, 370.08

(56) References Cited

U.S. PATENT DOCUMENTS

| | | | | |
|---|---|---|---|---|
| 3,703,639 A | * | 11/1972 | Raxhia et al. | 250/352 |
| 5,095,900 A | * | 3/1992 | Fertig et al. | 128/207.14 |
| 5,258,618 A | * | 11/1993 | Noble | 250/332 |
| 5,525,801 A | * | 6/1996 | Jackson et al. | 250/352 |
| 5,929,689 A | * | 7/1999 | Wall | 327/362 |

* cited by examiner

*Primary Examiner*—Constantine Hannaher
(74) *Attorney, Agent, or Firm*—Daniel J. Long; David W. Gomes

(57) ABSTRACT

A high resolution room temperature infrared camera requires no cryogenic cooling and high vacuum packaging, normally though necessary for infrared target detection, by using a "blind" polycrystalline lead salt resistor in combination with a matched active polycrystalline lead salt photoresistor both maintained at room temperature to provide a differential output indicative of an IR generating target. As a result of the matched components, the differential output nulls out the dark current which is the result of the ambient at the camera. The high degree of linearity associated with polycrystalline photoresistors permits fabrication of a differential detector where dark current in the active element is nulled out by equal and opposite current flow in a non-optically active reference resistor. Rather than a reference provided by a mechanical chopper normally used to correct for array non-uniformity, and rather than using costly temperature stabilization, the subject polycrystalline photoresistor provides a factory-setable reference, such that dark current can be canceled with the use of a nearly identical "blind" element beside the optically active element.

14 Claims, 5 Drawing Sheets

ROOM TEMPERATURE IR CAMERA

FIELD OF INVENTION

This invention related to infrared cameras, and more particularly to a room temperature infrared camera in which matched photoresistors are used in a differential mode to null out ambient-induced dark current.

BACKGROUND OF THE INVENTION

It will be appreciated that in a military context it is important to be able to identify an incoming missile due to its IR signature. The infrared signature must be discriminated from the background such that the missile is discernible from, for instance, a rock or sand dune which can reflect ambient sun light into the sensor aperture. In the past, wide angle infrared cameras have been proposed in which infrared cameras are placed about the tank so that incoming missiles can be spotted from any direction.

In order to accomplish robust target detection, it was thought that the only way to be able to differentiate the IR signature of an incoming missile from the background was to employ cryogenically-cooled detectors located in vacuum bottles so that the radiation from the target could be distinguished from background. Also it was thought that it would be necessary to provide a reference sensor and chop its output to provide a uniform background reference against which to compare IR detector outputs.

Also, in the past IR detectors have been made from single crystals such as InSb, and HgCdTe which respond to various red spike and blue spike characteristics of the incoming missile. Single crystal detectors require cryogenic cooling to meet sensor sensitivity requirements and tend to be too expensive for ground-vehicle self protection applications.

Note that, the purpose of using red spike and blue spike detection algorithms is to be able to distinguish the 4 micron missile radiation from radiation attributable to the surrounding background and solar reflections. Blue spike detection refers to detection in the 3.8–4 micron range, whereas red spike detection is usually in the 4.4–4.7 micron range.

In short, in the past cryogenically-cooled detectors with chopped reference signals have been tuned to the red spike and blue spike ranges in order to be able to distinguish an IR target from the surrounding terrain.

It will be appreciated that aside from the difficulty of providing a stable reference, the cryogenic and vacuum bottle requirements are such that infrared cameras have only been achievable at great cost. Not only are the cameras expensive due to the packaging required for the cryogenically-cooled thermos bottles in which an ultra high vacuum must be maintained and for which cryogenic refrigerators must be employed, maintenance for such a camera in the field is a large problem.

With a tank having 4 to 5 scanning infrared cameras, the cost of such an array of cameras plus processing makes such a non-room temperature solution impractical. Additionally, when field maintenance is added to the cost, the reliable cost-effective infrared camera is not presently available for use in the military arena.

In the civilian context, it is exceedingly desirable to have a wide angle infrared camera to be able to scan the output of, for instance, a sluice gate in a paper making machine to detect the degree of moisture in the sheet as it is being dried over the Fourdrinier wires. In the past, single pixel infrared detectors have been utilized to determine the moisture content of the web that is being dried.

However, the single point detectors do not take into account the fact that the web varied in moisture across its lateral extent. Controlling the rate at which paper is made based on a single infrared detector does not take into account the fact that the web itself is not uniform. It is therefore desirable to provide a wide angle infrared camera to detect the moisture content across the entire sheet to provide more precise process control.

It will thus be appreciated that infrared cameras operating in hostile environments are required in a variety of different applications such as steel making, and other processes such as plastic injection molding and pollution monitoring. In addition, such a camera could be employed for non-invasive glucose monitoring for diabetic patients.

SUMMARY OF THE INVENTION

Rather than providing a wide angle infrared camera with cryogenic cooling and vacuum apparatus, in the subject invention a room temperature wide angle infrared camera is provided through the utilization of photoresistors which have marked linearity in their response. The linearity stems from their polycrystalline nature and large boundary size. These photoresistors are located side by side, with the one photoresistor being the active photoresistor and with the other photoresistor being the "blind" photoresistor. As a result, the photoresistor elements are subjected to the same ambient temperature, with the so called "blind" photoresistor having its output subtracted from that of the active photoresistor to provide a differential output. This differential output is then utilized as the target indicating signal, with the ambient having been subtracted out at the photoresistor array. Note that, because of the linearity of the photoresistors, no chopped references or temperature stabilizers are required. The only thing that may be required is a thermo-electric heat sink at the back of the array to keep it at or near room temperature.

In one embodiment, accurate dark current nulling is provided through the utilization of a "blind" polycrystalline lead salt resistor matched to an active polycrystalline lead salt photoresistor. These devices exhibit a high degree of linearity over varying ambient temperatures that permits exact cancellation of the ambient due to the matched characteristics of the active photoresistor and its reference photoresistor, while at the same time providing a useable output to distinguish infrared target radiation from the surrounding terrain.

In one embodiment infrared photoresistors are tailored to two different wavelengths corresponding to the aforementioned red spike and blue spike by providing photoresistors having different lead salt compositions. To this end, a compact two color array is provided by stacking the photoresistors responding to a first wavelength on top of those responding to a second wavelength, with each set of photoresistors having companion and matching "blind" photoresistors to permit dark current cancellation.

Not only is this room temperature infrared camera of use in military applications, it may also be used for process control where the temperature of a wide expanse of material must be monitored. Papermaking and steelmaking are two examples.

It is even possible to overlay the array with a variable spectral filter so that different columns of the display can monitor different wavelengths thus to generate a temperature profile.

In summary, a high resolution room temperature infrared camera requires no cryogenic cooling and high vacuum packaging, normally thought necessary for infrared target detection, by using a "blind" polycrystalline lead salt resistor in combination with a matched active polycrystalline lead salt photoresistor both maintained at room temperature to provide a differential output indicative of an IR generating target. As a result of the matched components, the differential output nulls out the dark current which is the result of the ambient at the camera. The high degree of linearity associated with polycrystalline photoresistors permits fabrication of a differential detector where dark current in the active element is nulled out by equal and opposite current flow in a non-optically active reference resistor. Rather than a reference provided by a mechanical chopper normally used to correct for array non-uniformity, and costly temperature stabilization, the subject polycrystalline photoresistor provides a factory-setable reference, such that dark current can be canceled with the use of a nearly identical "blind" element beside the optically active element.

BRIEF DESCRIPTION OF THE DRAWINGS

These and other features of the subject invention will be better understood in connection with the Detailed Description in conjunction with the Drawings, of which.

DETAILED DESCRIPTION

Figure 1:
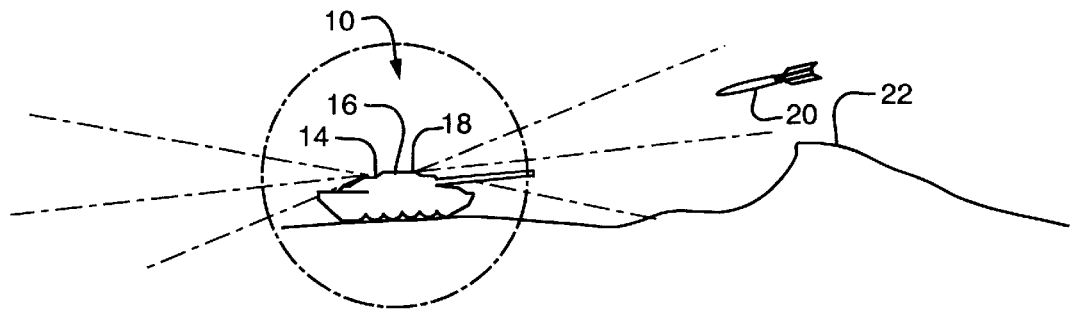
FIG. 1 is a diagrammatic representation of the typical military application for an infrared camera in which an incoming missile is depicted as approaching a tank provided with a number of infrared cameras.

Referring now to FIG. 1, in a typical military tactical situation a tank 10 is provided with a number of infrared cameras 14, 16, and 18, which are utilized to scan the horizon for an incoming military threat such as a missile 20. It is the purpose of the infrared cameras and the associated processing to be able to detect a missile 20 from radiation reflected from, for instance, a sand dune 22, which radiation constitutes reflected sunlight into the aperture of the IR camera.

Figure 2:
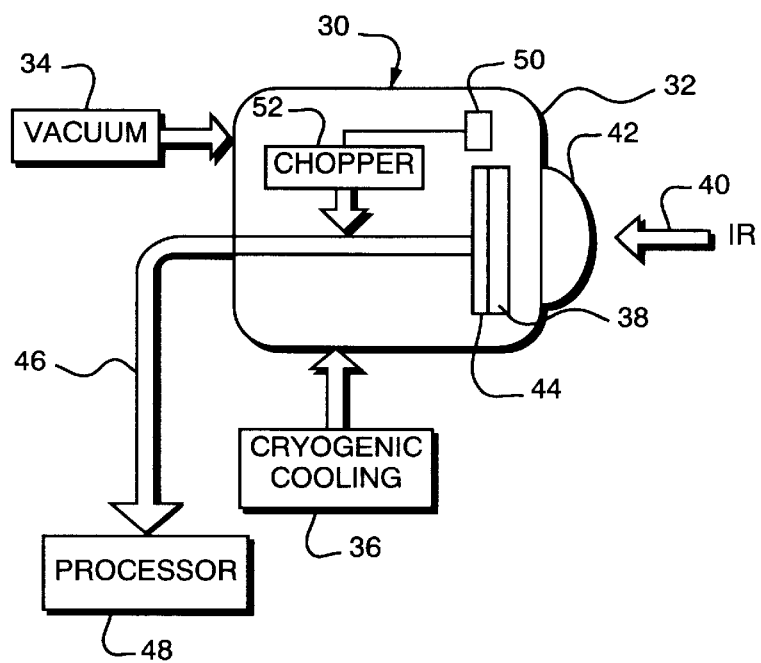
FIG. 2 is a schematic and block diagram of a prior art cryogenically-cooled infrared camera which utilizes a vacuum bottle and a chopped reference to be able to distinguish an incoming IR target from the surrounding terrain.

As illustrated in FIG. 2 a typical prior art infrared camera 30 is provided in a chamber 32 which is insulated so as to provide a vacuum bottle, with a vacuum 34 applied to the chamber. Cryogenic cooling 36 in the form of liquid nitrogen is provided to the chamber to cool the chamber down.

Inside camera 30 is a detector array 38, which typically is an array of single crystal photodetectors usually of an indium selenide or a mercury cadmium telluride variety to be able to detect radiation in the blue and red regions of the electromagnetic spectrum. The purpose of this red spike, blue spike detection is to be able to distinguish a target from the surrounding terrain.

Infrared radiation such as illustrated by arrow 40 is focused on array 38 via a lens or optical system 42, with the array being coupled to a readout integrated circuit or ROIC 44 which usually contains buffers, pre-amplifiers, capacitors and an output multiplexer. The output of the multiplexer is provided over a bus 46 to a processor 48 for processing the incoming target signatures to ascertain whether a threat exists or not.

In addition to providing a vacuum bottle and cryogenic cooling, a reference detector 50 was thought to be necessary, with its output being chopped by chopper 52 and compared to the output of the various elements of array 38 in order to be able to provide a uniform reference against which incoming radiation is to be compared.

As will be seen, not only must the cryogenic cooling be applied to the camera housing, and not only must the housing be evacuated to form a thermos bottle, it was thought that these precautions were not enough to be able to permit distinguishing an IR target from the surrounding terrain. As a result it was thought that only through the utilization of a chopped reference detector could one provide a sufficiently uniform response for the array to be able to detect an incoming missile.

Figure 3:
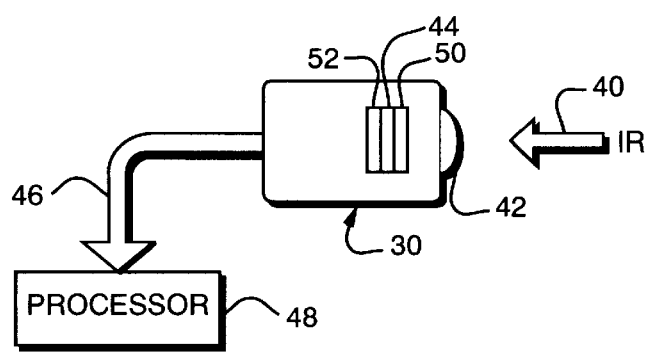
FIG. 3 is a block and schematic diagram of the subject room temperature infrared camera in which an array of photoresistors is provided with companion matched "blind" photoresistors to be able to cancel out dark current prior to the outputs being provided to a readout integrated circuit.

In counterdistinction to the cryogenically cooled and awkward infrared cameras of the past, in the subject invention a room temperature camera depicted in FIG. 3 is provided with an array 50 with each array element having an active photoresistor and a "blind" photoresistor. It is a feature of the subject invention that the currents from the active and "blind" photoresistors are connected in phase opposition. This provides a differential output which is the result of the incoming infrared radiation minus the ambient. What this means is that the so called "dark current" associated with photoresistors is canceled, thereby precluding the need for cryogenic cooling, vacuum packaging and in fact the utilization of a chopped reference.

Array 50, which will be described hereinafter, is connected to readout integrated circuit 44 which is a standard circuit available for infrared cameras. Array 50 and circuit 44 are in turn mounted on a thermo-electrically cooled heat sink 52, with the thermo-electric cooling being provided by reverse bias diodes as is common. The output of the readout integrated circuit is provided over bus 46 to processor 48 to be able to identify the existence of an IR target in the field of view of the camera.

Figure 4A:
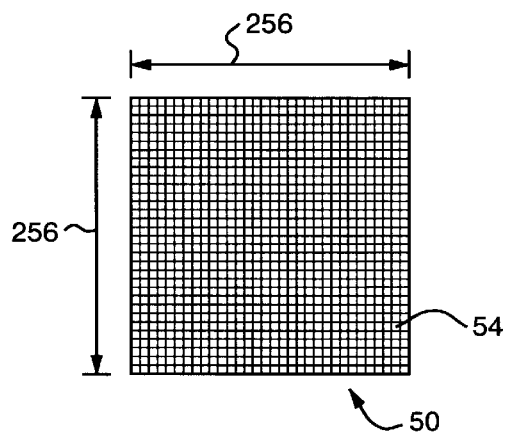
FIG. 4A is a diagrammatic and top view of an array of photoresistors onto which an infrared is to be imaged.

Referring now to FIG. 4A, in one embodiment an array of photodetectors is provided across a sheet 54, with the sheet providing a 256×256 array of photodetectors.

Figure 4B:
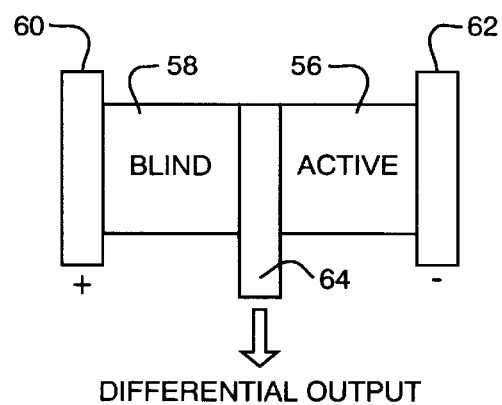
FIG. 4B is a diagrammatic representation of one of the elements of the array of FIG. 4A indicating a "blind" element and an active element.

As seen in FIG. 4B, each of the array elements includes an active element 56 and a "blind" element 58 which are matched such that when oppositely polarized DC power is applied across busses 60 and 62 a differential output is available at bus 64 which constitutes the difference between the active element being irradiated with infrared radiation and the "blind" element which has the incoming infrared radiation blocked.

Figure 4C:
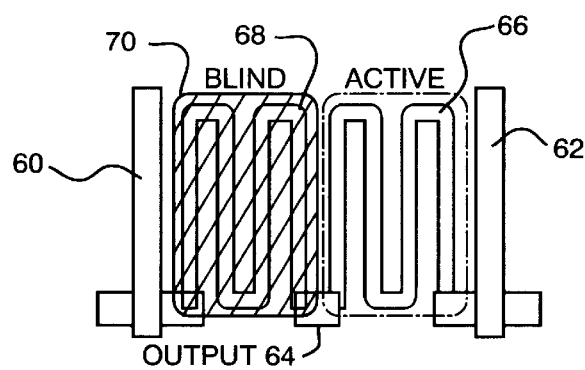
FIG. 4C is a top view of an element of the array of FIG. 4A indicating a serpentine "blind" element adjacent a serpentine active element, with the "blind" element covered with a shield such as a metal shield to prevent penetration of infrared radiation.

Such "blind" and active elements are illustrated in FIG. 4C in which the active element includes a serpentine stripe 66 of a polycrystalline lead salt, whereas the "blind" element 68 is a like serpentine photodetector. A metal mask 70 is placed over the "blind" element so as to prevent incoming infrared radiation from reaching the element.

Figure 4D:
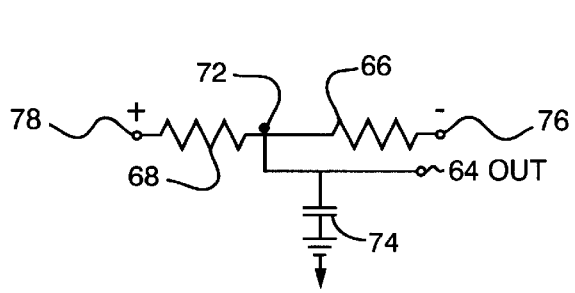
FIG. 4D is a schematic diagram of the elements of FIG. 4C indicating oppositely polarized "blind" and active elements, the junction of which is utilized as an output applied across a capacitor used for storage of the differential value.

Referring to FIG. 4D, the schematic equivalent is shown in which active photoresistor 66 is shown coupled to "blind" photoresistor 68 at a juncture 72 which provides a current across a capacitor 74, that stores the output available at 64 as illustrated. Note that photoresistor 66 is provided with a negative voltage as illustrated at 76, whereas "blind" photoresistor 68 is provided with a positive voltage as illustrated at 78.

Figure 4E:
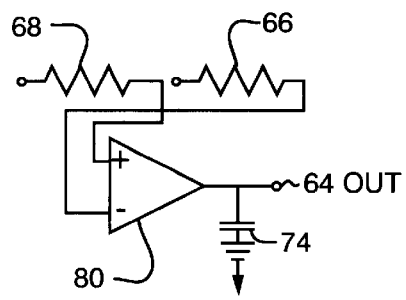
FIG. 4E is a schematic diagram of an alternative embodiment of the subject invention in which the "blind" and active elements are provided to a differential amplifier.

Referring now to FIG. 4E, active and "blind" photoresistors 66 and 68 may have their individual outputs provided to the differential inputs of a differential amplifier 80 the output of which is applied across capacitor 74. The use of a differential amplifier in an alternative embodiment permits more accurate signal cancellation and adjustment of voltages so that the output of the array can be made uniform across all of the elements.

Figure 5:
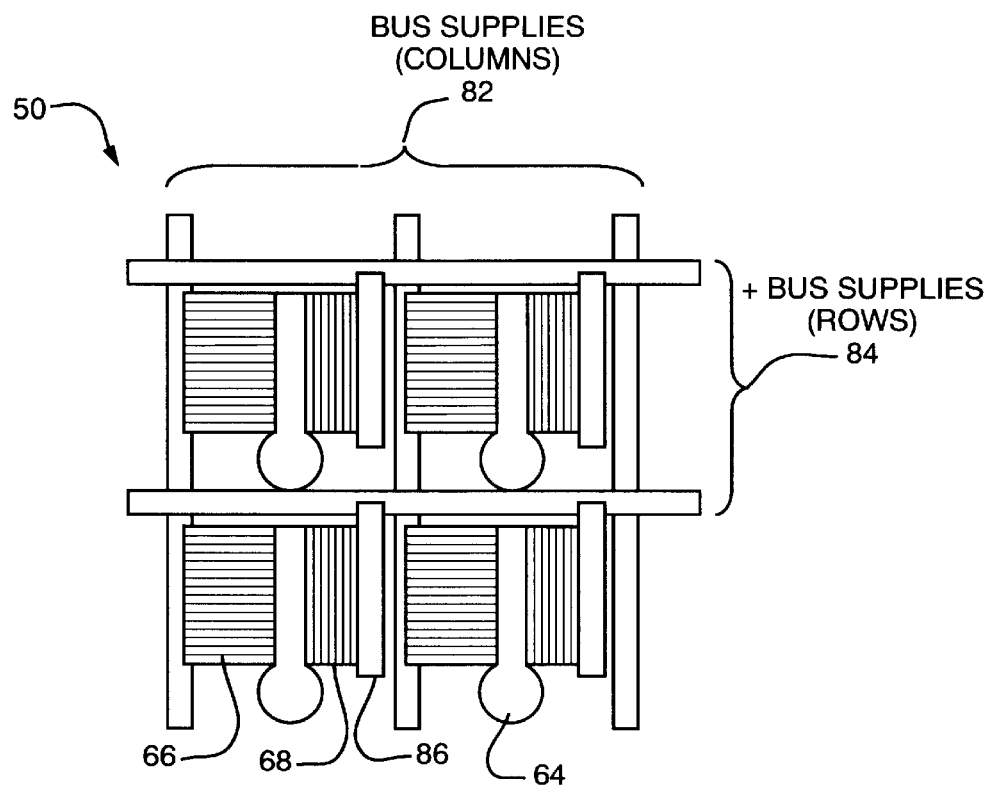
FIG. 5 is a top-top and schematic view of the bus structure necessary to support the "blind" and active elements of the array of FIG. 4A showing the bus supplies in orthogonal directions along with an ROIC input node for an underlying circuit.

Referring now to FIG. 5, the orthogonal bus structure is illustrated in which columns 82 constitute the negative bus supply, whereas rows 84 constitute the positive bus supply. Here active detector 66 has one side supplied with a negative voltage by bus 82, whereas "blind" detector 68 has a positive voltage supply to it through the utilization of a downwardly depending bus 86 such that the positive supply from row 84 is applied to the "blind" detector. Here the ROIC input node corresponds to output 64 of the element pair in FIG. 4C.

Figure 6A:
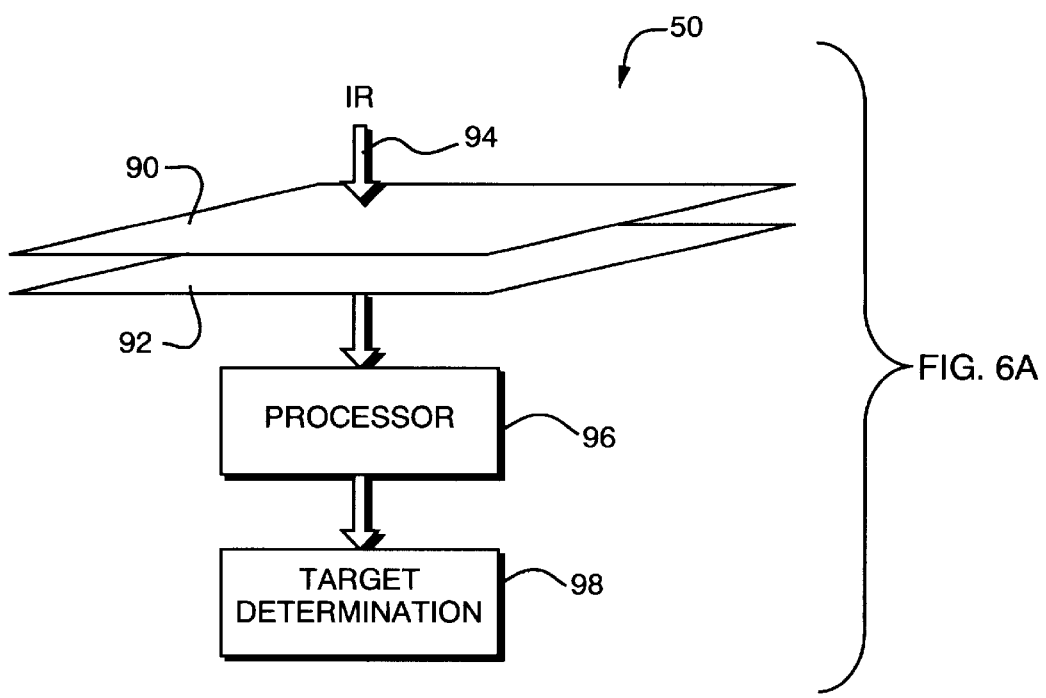
FIG. 6A is diagrammatic representation of the utilization of the red spike and green spike array along with a processor which utilizes the outputs of the red spike and green spike arrays to permit target determination.

Referring now to FIG. 6A, it will be appreciated that the array 50 of FIG. 5 may be divided up into a red spike array 90 and a blue spike array 92, which are stacked one on top of the other. More infrared radiation 94 passes through the red spike array to the blue spike array. The outputs are processed at 96 and a typical red spike, blue spike target determination is accomplished as illustrated at 98.

Figure 6B:
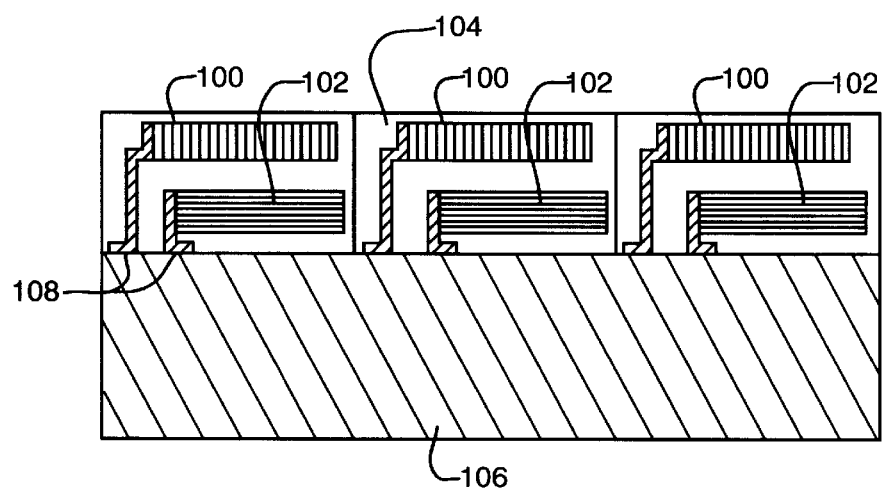
FIG. 6B is a diagrammatic and cross-sectional representation of the utilization of the two color stacked array on top of a CMOS ROIC in which the arrays are potted in CVD oxide, with each of the elements of each of the arrays having a dark current reference photoresistor to be able to cancel out the dark current.

How this is accomplished can be seen as illustrated in FIG. 6B, in which elements 100 of a top array are positioned above elements 102 of a bottom array, with the elements being potted in a CVD oxide 104 as illustrated. It will be appreciated that each of the elements 100 and 102 are in fact bifurcated elements in which one element of the pair is "blind" and the other is active. The elements are positioned at a typical read out circuit diagrammatically illustrated 106, with the inputs to circuit 106 being as illustrated at 108. The result is a robust array configuration which can be mounted on a thermo-electrically controlled heat sink to provide for room temperature infrared target acquisition. It is noted since the elements are constructed using polycrystalline lead salts, sensitivity is not degraded by room temperature operation due to the polycrystalline structure and due to the linearity between the array elements which permit for dark current cancellation.

Figure 7:
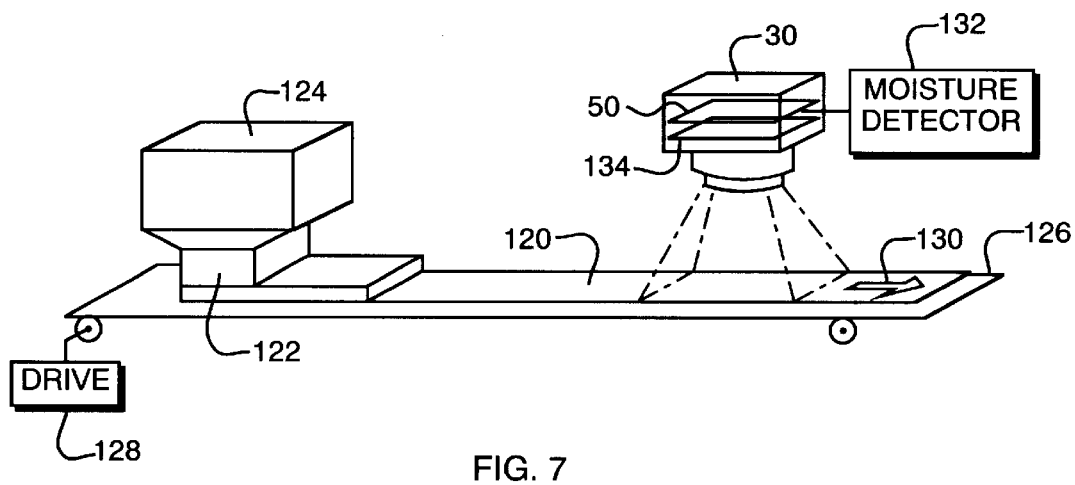
FIG. 7 is a diagrammatic representation of the utilization of an infrared camera in combination with a variable spectral filter to monitor the moisture content of a web which emanates from a sluice gate onto a Fourdrinier wire so as to be able to control web speed; and, FIG. 8 is a diagrammatic representation of a variable spectral filter having columns responding to different wavelengths in combination with columns of underlying array utilized to be able to provide a spectral response for the various colors involved in the spectral filter.

Referring now to FIG. 7, in a commercial application for process control, infrared camera 30 having the subject array 50 therein is utilized to detect the moisture of a web 120 produced at a sluice gate 122 having a hopper 124 thereabove into which is loaded pulp for papermaking. The web is formed over a Fourdrinier wire 126 driven by a drive 128 in the direction of arrow 130. It is important to be able to detect the moisture content of web 120 to be able to control the speed of drive 128, and to this end a moisture detector 132 is coupled to camera 30. In order to determine moisture content a variable spectral filter 134 is placed in the focal plane of camera 50 so that the camera detects IR radiation to determine moisture content of the web in a number of wavelengths.

Figure 8:
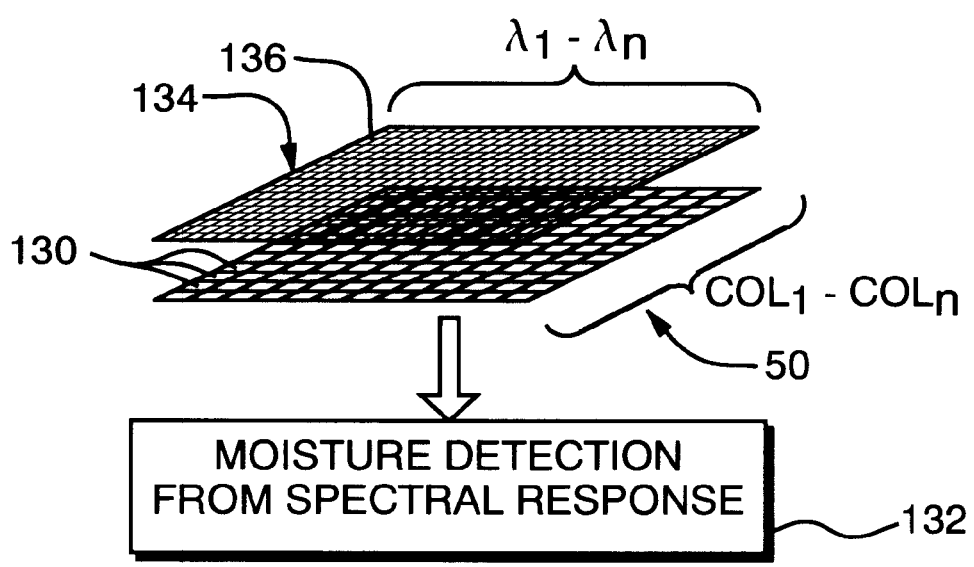

Referring now to FIG. 8, variable spectral filter 134 may be provided with a number of columns 136 each providing filtration at a given wavelength. Underneath the filter is array 50 in which columns 138 of the array detect infrared radiation of a different wavelength as determined by variable spectral filter 134. In techniques which are well know, radiation at a number of wavelengths permits moisture detection from the spectral response as illustrated at 132.

In summary, what is provided is a room temperature infrared camera which provides the ability to sense and discriminate infrared radiation from a background without the use of cryogenic, vacuum and chopped reference techniques. The camera can thus be used both in the military context for protecting vehicles and in the process control context for determining, for instance, moisture content or spectral profiles for any material or device being manufactured.

Having now described a few embodiments of the invention, and some modifications and variations thereto, it should be apparent to those skilled in the art that the foregoing is merely illustrative and not limiting, having been present by the way of example only. Numerous modifications and other embodiments are within the scope of the ordinary skill in the art and are contemplated as falling within the scope of the invention as limited only by appended claims and equivalents thereto.

What is claimed is:

1. A high resolution wide angle infrared camera operating at room temperature, comprising:
    an integrated array having a plurality of infrared detectors, each of said detectors including a matched pair of photoresistors in close proximity to each other, one of the photoresistors in said pair being an active photoresistor, and the other photoresistor of said pair being a blind photoresistor, wherein said blind photoresistor is shielded from incident infrared signals;

means for connecting each said pair of photoresistors so as to provide a differential output thereby canceling a dark current, wherein said differential output is applied across an integration capacitor;

optics for focusing an infrared signal onto said integrated array;

a readout integrated circuit coupled to said infrared detector array for providing a multiplexed output corresponding to the differential outputs of said photoresistors; and a processor for scanning and processing said multiplexed output from said readout integrated circuit.

2. The wide angle infrared camera of claim 1, and further comprising a heat sink coupled to said readout integrated circuit.

3. The wide angle infrared camera of claim 2, further comprising a thermo-electric cooler at said heat sink for maintaining said infrared detector array at room temperature.

4. The wide angle infrared camera of claim 1, wherein said means for connecting further comprises a differential amplifier coupled to said active photoresistor and said blind photoresistor, wherein said differential amplifier provides said differential output to said capacitor.

5. The wide angle infrared camera of claim 1, wherein said means for connecting is by coupling said active photoresistor and said blind photoresistor with oppositely polarized DC power.

6. The wide angle infrared camera of claim 1, wherein said blind photoresistor is shielded by a metal shield.

7. The wide angle infrared camera of claim 1, wherein each of said photoresistors are arranged in serpentine stripes.

8. The wide angle infrared camera of claim 1, further comprising an orthogonal bus structure having a row bus supply and an column bus supply coupling said plurality of detectors, wherein said row bus supply and said column bus supply are oppositely polarized.

9. A high resolution wide angle infrared camera operating at room temperature, comprising:

a one or more wavelength specific integrated arrays having a plurality of infrared detectors mounted upon each of said arrays, wherein each of said detectors includes a matched pair of photoresistors, one of the photoresistors in said pair being an active photoresistor, and the other photoresistor of said pair being a blind photoresistor, and wherein said blind photoresistor is shielded from incident infrared signals;

means for connecting each said pair of photoresistors so as to provide a differential output thereby canceling a dark current, wherein said differential output is applied across a capacitor;

optics for focusing an infrared signal onto said one or more integrated arrays;

a readout integrated circuit coupled to said infrared detector array for providing a multiplexed output corresponding to the differential outputs of said photoresistors; and a processor for scanning and processing said multiplexed output from said readout integrated circuit.

10. The wide angle infrared camera of claim 9, wherein one of said wavelength specific integrated arrays is a red spike array.

11. The wide angle infrared camera of claim 9, wherein one of said wavelength specific integrated arrays is a blue spike array.

12. The wide angle infrared camera of claim 9, wherein one of said wavelength specific integrated arrays is a red spike array and another said wavelength specific integrated arrays is a blue spike array, and wherein said red spike array is stacked in a planar relationship to said blue spike array with said red spike array being first to receive said infrared signal.

13. The wide angle infrared camera of claim 9, further comprising a variable spectral filter adjacent said wavelength specific integrated arrays passing a filtered output of said infrared signal to said integrated arrays.

14. The infrared camera of claim 13, wherein said variable spectral filter includes a planar material having columns, wherein each column has a different spectral transmissivity.

* * * * *